United States Patent [19]
Casey

[11] Patent Number: 5,846,255
[45] Date of Patent: Dec. 8, 1998

[54] SURGICAL CLIP

[75] Inventor: Donn Casey, Cambridge, United Kingdom

[73] Assignee: Casey Medical Products Limited, Cambridge, United Kingdom

[21] Appl. No.: 701,661

[22] Filed: Aug. 22, 1996

[30] Foreign Application Priority Data

Jan. 31, 1996 [GB] United Kingdom .................... 9601966

[51] Int. Cl.⁶ .................................................. A61B 17/08
[52] U.S. Cl. ........................... 606/157; 606/151; 606/120
[58] Field of Search ............................ 606/151, 157–158, 606/120, 201; 604/250, 346; 24/460, 461, 462

[56] References Cited

U.S. PATENT DOCUMENTS 4,822,348  4/1989  Casey .

4,942,886  7/1990  Timmons ................................. 128/885
5,423,831  6/1995  Nates ....................................... 606/120
5,575,802  11/1996  McQuilkin et al. ..................... 606/151

FOREIGN PATENT DOCUMENTS 2 190 297  of 0000  United Kingdom .

Primary Examiner—Michael Buiz
Assistant Examiner—Tina T. D. Pham
Attorney, Agent, or Firm—Larson & Taylor

[57] ABSTRACT

A surgical clip has a resilient pad in a recess in one face and a hinged tongue on the other face, which face preferably presents no acute edge. The provision of a pad on only one face is found to produce a surprising improvement in effectiveness of the clip. In addition, the pad may be thicker and may be placed in a recess in one jaw, which can simplify manufacture while reducing the overall size of the clip.

17 Claims, 5 Drawing Sheets

SURGICAL CLIP

BACKGROUND OF THE INVENTION

This invention relates to clips for use in surgical procedures, particularly but not exclusively for human female sexual sterilisation by occlusion of the Fallopian tubes, or for clamping the blood vessels and other pedicles of the uterus during hysterectomy.

SUMMARY OF THE PRIOR ART

Amongst known clips for use in sterilisation is the Bleier clip consisting of a pair of plastics (e.g. polypropylene) jaws hinged together and having a catch for fastening the jaws together. The body duct to be occluded is gripped by the hard and unyielding plastics material of which the clip is made, which may result in poor healing of the stumps on each side of the clip and possible failure of the sterilisation.

To address this problem, clips such as those shown in GB2190297 and U.S. Pat. No. 4,822,348 were devised. Made of plastics, these have cushioning pads adhesively secured to each face of the jaws so as to clamp the duct less aggressively and encourage better healing of the stumps whilst still achieving effective occlusion. Whilst these clips offer advantages, the high cost often precludes their use in less developed countries.

These clips moreover are deep in section, requiring an undesirably large cannula to permit the introduction of the clip through the abdominal wall during keyhole surgery.

It is an object of the invention to overcome the above drawbacks, and to provide a surgical clip which is reliable but cost-effective, and can be deployed without undue difficulty.

SUMMARY OF THE INVENTION

One aspect of the present invention seeks (at least in its preferred embodiment) to address these problems. The present applicant has found surprisingly that satisfactory healing can be achieved by the use of a compressible pad on one only of the jaws.

Thus in a first aspect the invention provides a clip for surgical procedures comprising first and second jaws hinged together, and means for fastening the jaws together in a closed position, the first only of the jaws having a resilient pad opposing the second jaw.

In another aspect, the invention provides a clip for use in surgical procedures comprising first and second jaws hinged together, means for fastening the jaws together in a closed position, the first only of the jaws having a deformable pad on a face directed towards the second jaw so as in use to cushion or resiliently compress a duct or other body tissue held in the clip, an opposing face of the second jaw being configured to present no acute edge to said tissue when the jaws are closed.

By placing a pad on one jaw only, the overall depth of the clip can be reduced. This is so even if the pad is made thicker than either of the pads used in the known clips described above. Furthermore, the increased depth of a single pad allows it to be housed in a recess in its supporting jaw, and retained with the use of only a small quantity of adhesive elastomer or in some applications just mechanically. The pads can be moulded separately and assembly is much simpler compared with pads of known clips which are moulded in situ to the jaws.

The effect of closing a clip on a duct may be to tend to eject it from the clip. Therefore, the second jaw may have a tongue protruding from the opposing face towards the first jaw and away from the hinge such that the tongue retains said body tissue between the jaws, the tongue being moveable towards said second jaw upon closure of the clip.

In a first embodiment, a curved resilient tongue is provided on the second jaw, the tongue having an end located away from the hinge which is moveable towards the second jaw on closure of the clip. This may provide a simple but effective arrangement for trapping body tissue prior to closure of the clip. Surprisingly, the provision of a resilient tongue without a compressible pad positioned opposite a compressible pad has been found to provide better occlusion of a duct such as a fallopian tube without damage than was possible with a compressible pad on both surfaces, and may also enable a clip having a smaller overall size to be used.

For ease of manufacture and reliable occlusion, it is desirable for the compressible pad to be located in a recess in the jaw opposite the resilient tongue, the resilient tongue preferably being substantially less compressible than the compressible pad. Thus in a further aspect of the same inventive concept, there is provided a surgical clip comprising first and second jaws hinged together, means for fastening the jaws together in a closed position, a compressible pad provided on the first jaw only, preferably in a recess therein, and a resilient (curved) tongue integrally formed with the second jaw and biased so as to project towards the compressible pad on the first jaw and away from the hinge whereby in use to retain between the jaws when open a duct or other body tissue to be gripped by the clip.

With some arrangements, there may be a tendency for the end of the curved tongue to dig in to the duct. In a second embodiment of the invention this is avoided by hingedly mounting the tongue from the jaw rather than having it spring therefrom.

Thus in a still further aspect of the same inventive concept, there is provided a surgical clip comprising first and second jaws hinged together, means for fastening the jaws together in a closed position and a tongue hinged to the second jaw and biased so as to project towards the first jaw and away from the hinge whereby in use to retain between the jaws when open a duct or other body tissue to be gripped by the clip.

The tongue may be shaped so that on closure of the clip the tongue nests in a recess in the second jaw.

The tongue may be straight and when nested may form a continuous flat surface with the surface of the second jaw. The hinge may be deformable to permit said movement upon closure of the clip. Thus it may be a plastic hinge.

The hinged tongue may be employed in clips for surgical procedures other than sterilisation, for example in hysterectomy as mentioned above.

Fastening means may be positioned at or near the open end of the jaws remote from their hinged connection. By placing the fastening means remotely from the hinge the jaws are not required to act as cantilevers, and there are lesser loads on the fastening means than in the clips of the above-mentioned GB and US specifications since the mechanical advantage of the fastening means about the hinge is much greater in the present invention. Because the maximum bending moment on the jaws for a given clamping force is reduced compared to the prior art, the load-bearing cross-sectional depth of the jaws may be reduced, enabling the recess in the first jaw to be deeper and accommodate a deeper, and thus more effectively cushioning, pad. Alternatively the overall height of the clip may be reduced.

A surface of the resilient pad facing towards the second jaw may be inclined away from the second jaw towards the hinge. The base of the recess may be similarly inclined, and the resilient pad may be of constant thickness and width.

The fastening means may comprise a pair of spaced lugs at the end of the said first jaw, the second jaw having a portion which is located between said lugs when the clip is closed.

An embodiment of the invention now will be described merely by way of example with reference to the accompanying drawings, in which:

DESCRIPTION OF PREFERRED EMBODIMENTS

Figure 1:
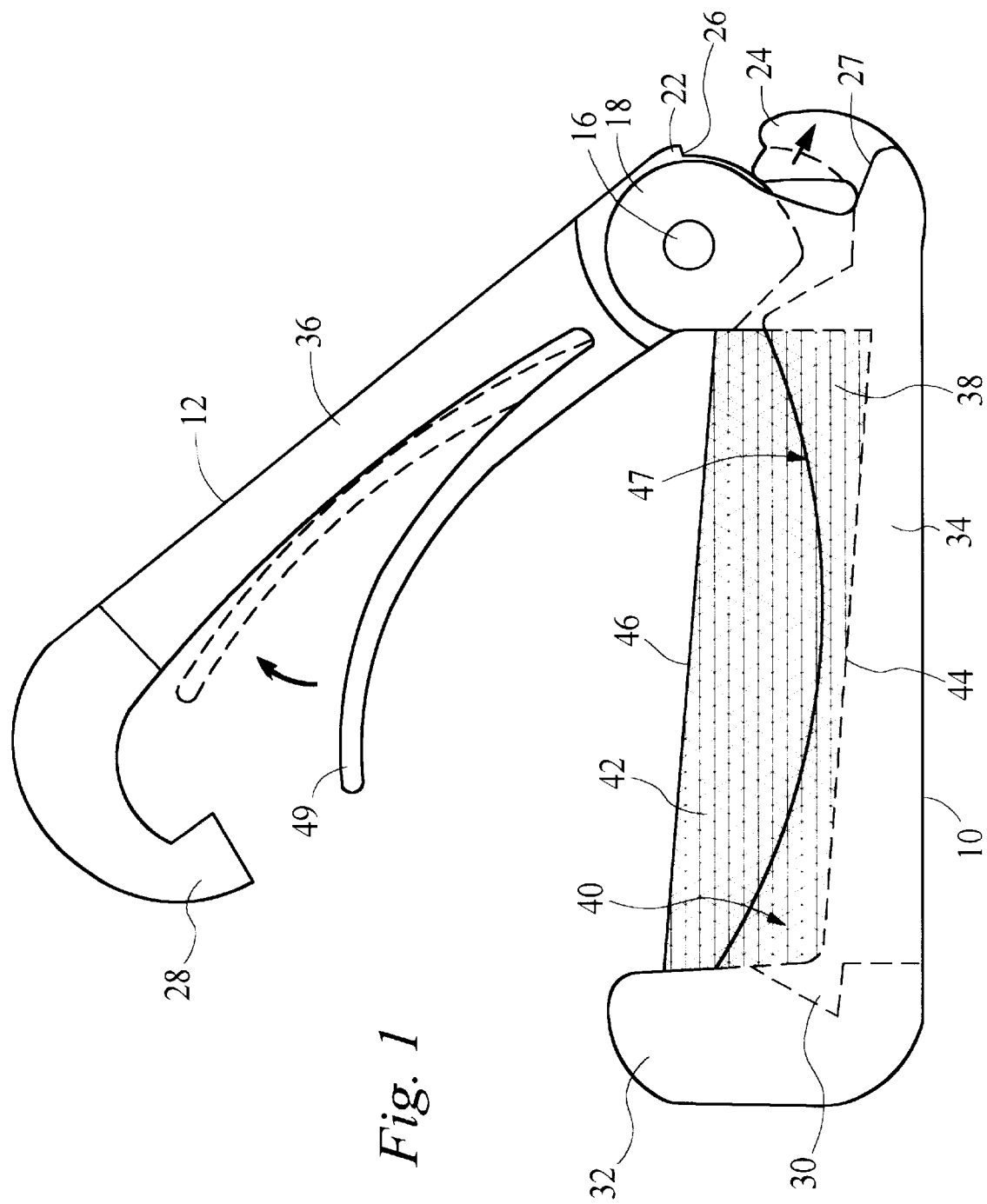
FIG. 1 is a side view of a first embodiment of the invention.
Figure 2A:
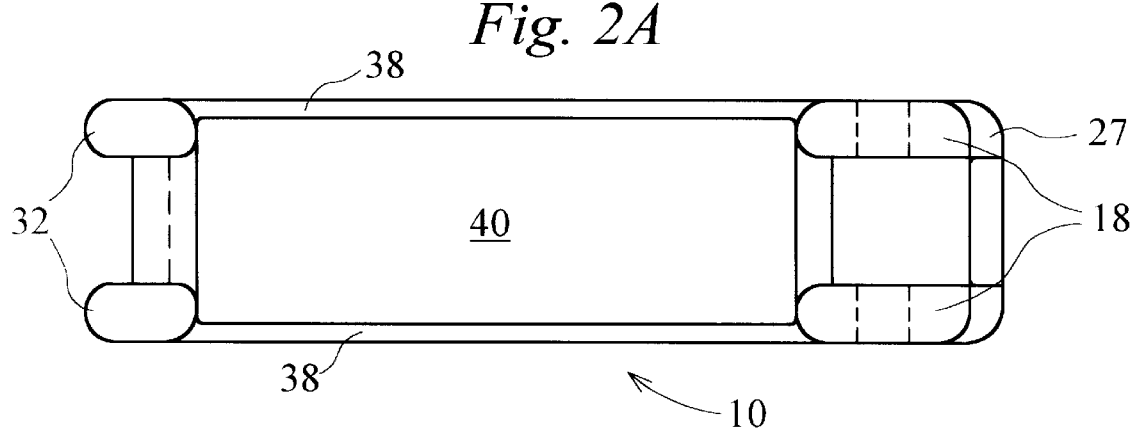
FIG. 2A is a plan view of a clip according to a first or second embodiment of the invention.
Figure 2B:
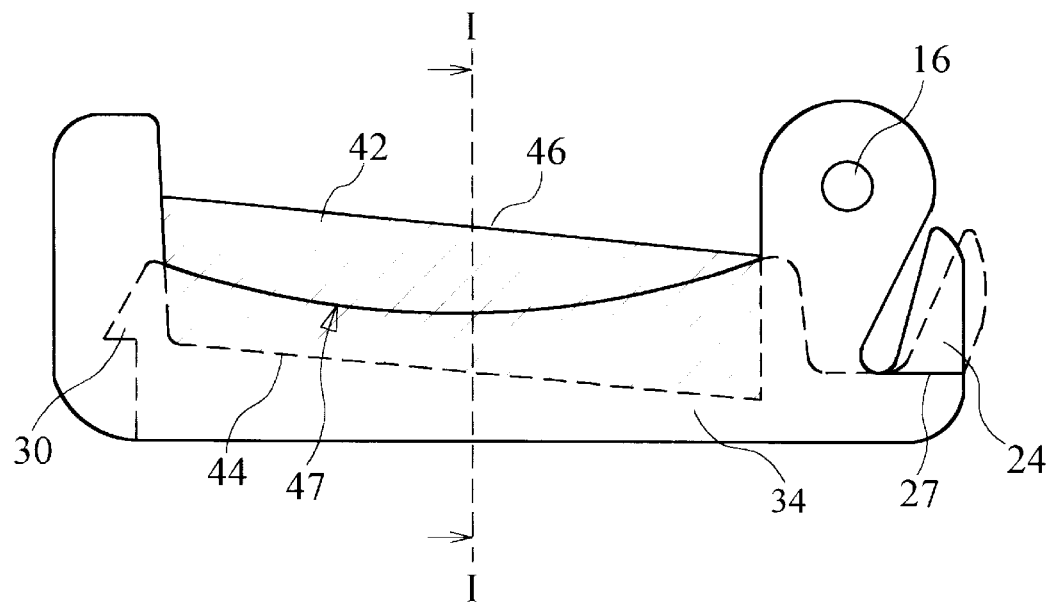
FIG. 2B is a side view of the clip of FIG. 2A.
Figure 2C:
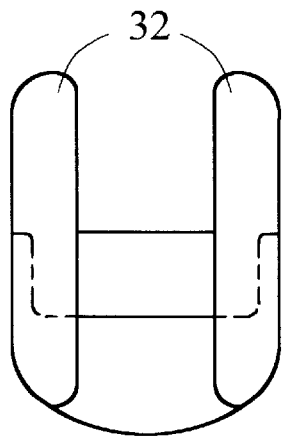
FIG. 2C is an end view of the clip of FIG. 2A (seen from the left of FIG. 2B)
Figure 2D:
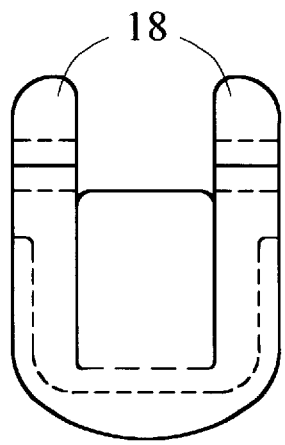
FIG. 2D is an end view of the clip of FIG. 2A (seen from the right of FIG. 2B)
Figure 2E:
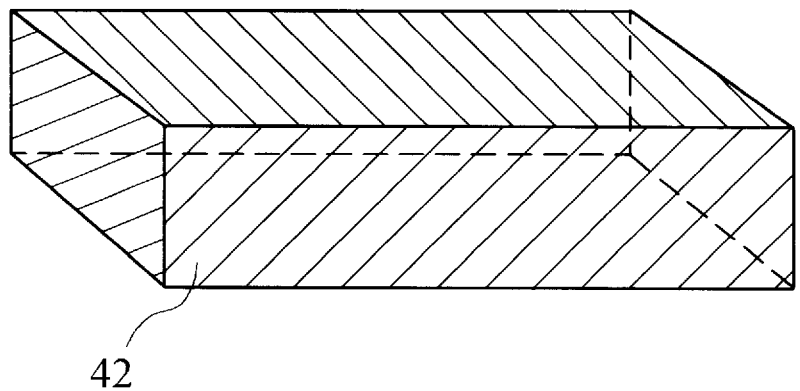
FIG. 2E is a three-dimensional view of a pad.
Figure 2F:
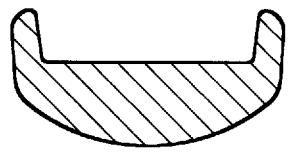
FIG. 2F is a cross sectional view taken along line I—I in FIG. 2B.

Referring first to FIGS. 1 and 2A–2F, a first embodiment of a surgical clip for use in human sterilisation comprises a first (lower) jaw 10 and a second (upper) jaw 12 of a plastics material advantageously polycarbonate. The jaws are hinged together by a titanium pin (not shown) which is a press fit in a bore 16 in lug 18 of the lower jaw and a running fit in a slightly larger bore 20 in a lug 22 of the upper jaw. A finger 24 at the rear of the lower jaw bears against a rear curved cam surface of the lug 22 so as to hold the jaw in a normally open position. The jaws are closed by compressing them together with sufficient force to deform the finger 24. A step on notch 26 in the camming surface limits the extent to which the jaws may be opened. Advantageously, the finger 24 and the camming surface, may be lubricated with biologically compatible silicone oil.

Platforms 27 are provided at the hinge end of the lower jaw for engagement with apparatus for applying the clip to a duct or other tissue.

At the end remote from the hinge, the jaws carry complementary fastening parts comprising a resiliently deformable spike 28 with a hook-shaped end, and a corresponding hook-shaped portion 30 on the lower jaw between upstanding lugs 32 which receive the spike 28 and stabilise the jaws when the clip is closed. The stiffness of the spike may be made such that when the hook portions engage each other there is a distinctly audible click or snap, indicating proper closure of the clip. The end of the spike 28 is sharp to assist in penetrating body tissue, for example when it is required to apply the clip to a duct to which is attached a membrane.

The main load bearing or beam portion 34, 36 of the upper and lower jaws are relatively thin-section compared to (say) those of U.S. Pat. No. 4,822,348 because the fastening means 28, 30 is remote from the hinge and thus the jaws do not have to act as cantilevers when the clip is closed.

The lower jaw has the side wall 38 extending between the lugs 32 and 18 to define a deep recess 40 in which a rectangular pad or block 42 of resilient cushioning material is received. Transverse walls between the pairs of lugs 18, 32 further define the recess. The base 44 of the recess 40 is inclined towards the hinge 18, 22 so as to diverge from the opposing face of the upper jaw. Consequently when the pad 42 is fully seated in the recess it is deformed into a non-rectangular parallelepiped shape as can be seen in FIG. 1, and its upper surface 46 is similarly inclined towards the hinge. This inclination of the surface assists in encouraging a duct to be gripped by the clip to move towards the inner (hinge) end of the clip.

The pad of a known biologically compatible soft silicone elastomer adhesive, e.g. of Shore hardness 20, is moulded to the required shape. It is secured in the recess a layer of the same adhesive. The pad is preferably between 2 and 4 mm thick; a thickness of about 3 mm has been found to give optimum results in many applications.

The upper surfaces 47 of the walls 38 are curved downwards so as to provide for adequate compression of the pad when cushioning a gripped duct without the walls 38 contacting the duct and crushing it.

To inhibit ejection of the duct or bodily tissue from the clip on closure, a curved tongue 49 of resilient material, typically integrally moulded with the remainder of the upper jaw, is provided. This traps the duct to be occluded on partial closure of the clip, and when the clip is fully closed is pressed flat against the upper jaw 36, assuming a configuration similar to that shown in the dashed lines in FIG. 1. Thus, pressed against the jaw 36, the curved tongue 49 is relatively incompressible, and serves to compress the duct or other tissue against the pad 42. The operative surface 48 is generally flat so as not to present any acute edges to tissue held in the clip when the clip is in its closed position. As can be seen in FIG. 1, the curved tongue 49 is generally of a lesser thickness than the load bearing portion of the upper jaw 36.

Figure 3A:
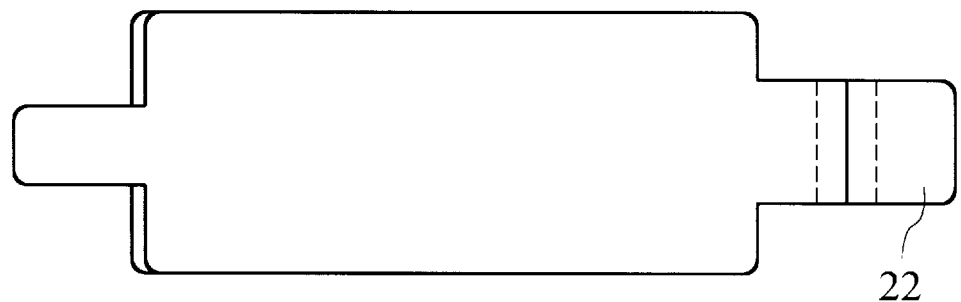
FIG. 3A is a plan view of a clip according to a second embodiment of the invention.
Figure 3B:
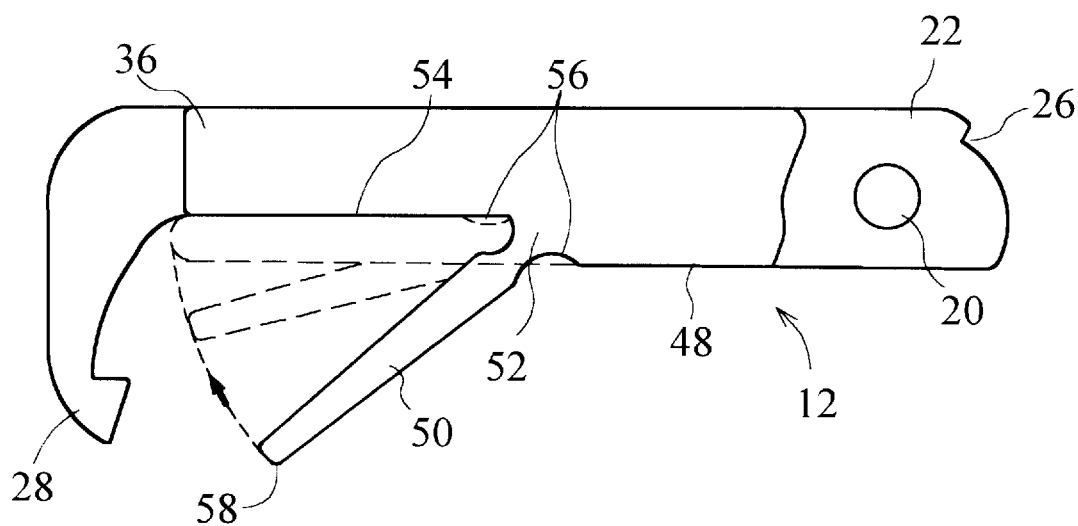
FIG. 3B is a side view of the clip of FIG. 3A.
Figure 3C:
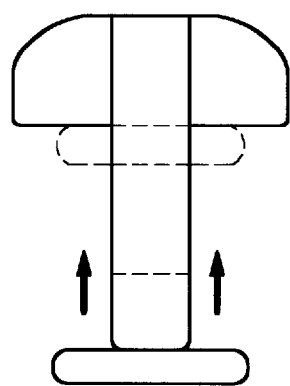
FIG. 3C is an end view of the clip of FIG. 3A (seen from the left of FIG. 3B)
Figure 3D:
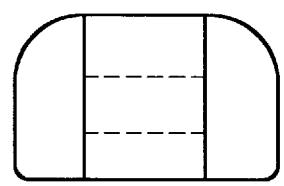
FIG. 3D is an end view of the clip of FIG. 3A (seen from the right of FIG. 3B)
Figure 3E:
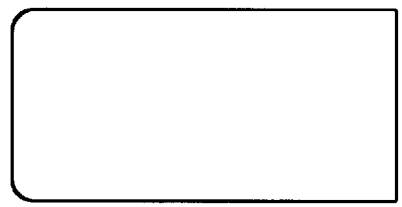
FIG. 3E is a plan view of a tongue of an upper jaw.

Referring to FIGS. 3A–3E, a second embodiment will now be described. The lower jaw is the same as in the first embodiment and will not be described further. In this embodiment, as in the first, the upper jaw 12 is not provided with any cushioning material, and its operative surface 48 is flat. This embodiment does not have a curved tongue 49; whilst the curved tongue without a cushioning pad works well for many applications, there may be some tissues where another arrangement is desirable. In the second embodiment, in place of the curved tongue 49, included in the operative surface is a hinged flap or tongue 50. This tongue is relatively rigid, and is biased towards an inclined position as shown in FIG. 3B by a deformable hinge 52, formed by a section of material of reduced thickness. When the clip is placed around a duct to be occluded the tongue serves to capture the duct and prevent it moving out from between the jaws as the clip is closed. Upon progressive closure of the clip, the hinge 52 deforms so that when the clip is closed the tongue 50 nests in a recess 54 in the upper jaw. The material of the jaw may be undercut or thinned e.g. at 56 to assist in close nesting of the tongue, whilst achieving an appropriate stiffness in the hinge. The hinge must be adequately stiff for the tongue to capture the duct, but compliant enough to allow the tongue to fold flat on closure. The end 58 of the tongue preferably is rounded so as to reduce any possibility of it digging in to tissue in the clip.

Being for use in human sterilisation the clip is appropriately dimensioned. Typically it is about 15 mm long and 4 mm wide; these dimensions are indicative rather than prescriptive.

When the clip is closed the Fallopian tube is gently cushioned and compressed between the face 48, the curved resilient tongue 49 (deformed against the upper jaw) or hinged tongue 50 (now flattened into its recess 54) and the pad 42. This gentle pressure causes excellent healing of the tube on each side of the clip into sealed stumps 5 and the poor healing or severing of the tube which is possible with jaws of hard plastics material is avoided.

Each feature disclosed in the specification (which term includes the claims) and/or shown in the drawings may be incorporated in the invention independently of other disclosed and/or illustrated features.

The text of the abstract filed herewith is hereby deemed to be repeated here in full as part of the specification.

I claim:

1. A clip for surgical procedures comprising first and second jaws hinged together, and a fastening arrangement for fastening the jaws together in a closed position, the first only of the jaws having a resilient pad opposing the second jaw, the pad being disposed in a recess defined by walls projecting from a primary load-bearing section of the first jaw.

2. A clip as claimed in claim 1 wherein the clip is configured so as, in use, to resiliently compress a duct or other body tissue held in the clip, and wherein an opposing face of the second jaw is configured to present no acute edge to the duct or tissue when the jaws are closed.

3. A clip as claimed in claim 1, wherein the second jaw has a tongue protruding from the opposing face towards said first jaw and away from the hinge so as, in use, to retain a duct or other body tissue between the jaws, the tongue being moveable towards said second jaw upon closure of the clip.

4. A clip as claimed in claim 3 wherein the tongue is resiliently deformable towards the said second jaw upon closure of the clip.

5. A clip as claimed in claim 4 wherein the tongue is integrally formed with said second jaw.

6. A clip as claimed in claim 1 wherein the first and second jaws are hinged together at a hinge, said first jaw has a longitudinal axis and the pad has an inclined surface which faces the second jaw, which is inclined at an angle with respect to the longitudinal axis of the first jaw and which slopes from said hinge away from said longitudinal axis.

7. A clip as claimed in claim 6 wherein the recess in which the pad is disposed has a base having an inclined surface extending substantially parallel to said inclined surface of said pad.

8. A clip as claimed in claim 1 wherein the resilient pad is of constant thickness and constant width.

9. A clip as claimed in claim 1, dimensioned for use in human female sexual sterilization, wherein the jaws are arranged to trap a fallopian tube.

10. A clip as claimed in claim 1 further comprising a curved tongue integrally formed with the second jaw and biased so as to project towards the first jaw and away from the hinge, whereby, in use, to retain, between the jaws, when open, a duct or other body tissue to be gripped by the clip.

11. A clip as claimed in claim 10 wherein the curved tongue is of a lesser thickness than a load-bearing portion of the second jaw so that on closure of the clip, the tongue is deformed in preference to the load-bearing portion of the second jaw.

12. A clip as claimed in claim 10 wherein the tongue is shaped such that, on closure of the clip, the tongue abuts against a load-bearing portion of the second jaw to transmit a compressive force from said load-bearing portion of the second jaw to a duct or body tissue in the clip.

13. A clip as claimed in claim 1 wherein the fastening arrangement is configured to provide an audible indication of correct closure of the clip.

14. A clip as claimed in claim 1 wherein the first and second jaws are hinged together at a hinge at one end of the jaws and the fastening arrangement is disposed at least near to the opposite end of the jaws remote from the hinge.

15. A clip as claimed in claim 1 wherein the fastening arrangement comprises a pair of spaced lugs at one end of the said first jaw.

16. A clip as claimed in claim 1 wherein the jaws are pivotable about a hinge between a closed and fully open state, said clip further comprising a projection extending from an end of the second jaw proximate said hinge and abutting the first jaw so as to prevent further opening of the jaws.

17. A clip for surgical procedures comprising first and second jaws hinged together, and a fastening arrangement for fastening the jaws together in a closed position, the first only of the jaws having a resilient pad opposing the second jaw, the second jaw including a tongue, said tongue protruding from a face of the second jaw opposing the first jaw and away from a hinge joining the two jaws, whereby, in said closed position, a duct or other body tissue can be retained between said resilient pad and said tongue, the pad being disposed in a recess, and the recess being defined by walls projecting from a primary load-bearing section of the first jaw.

* * * * *